United States Patent [19]

Marvola et al.

[11] Patent Number: 5,849,330
[45] Date of Patent: *Dec. 15, 1998

[54] CONTROLLED RELEASE PHARMACEUTICAL

[75] Inventors: Martti Lauri Antero Marvola, Helsinki; Taina Sirkiä, Vantaa, both of Finland

[73] Assignee: Orion-yhtymä Oy, Espoo, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 611,552

[22] Filed: Mar. 6, 1996

Related U.S. Application Data

[63] Continuation of Ser. No. 199,312, filed as PCT/FI92/00242, Sep. 16, 1992 published as WO93/05769, Apr. 1, 1993, abandoned.

[30] Foreign Application Priority Data

Sep. 17, 1991 [FI] Finland .................................... 914354

[51] Int. Cl.$^6$ ........................................................ A61K 9/24
[52] U.S. Cl. ................................................ 424/472; 424/471
[58] Field of Search ................................... 424/472, 474, 424/480, 490, 494, 471, 469, 470

[56] References Cited

U.S. PATENT DOCUMENTS

| | | | |
|---|---|---|---|
| 2,809,917 | 10/1957 | Hermelin | 424/472 |
| 3,048,526 | 8/1962 | Boswell | 424/472 |
| 3,317,394 | 5/1967 | Fryklof et al. | 424/472 |
| 3,388,041 | 6/1968 | Gans et al. | 424/464 |
| 3,558,768 | 1/1971 | Klippel | 424/485 |
| 4,122,157 | 10/1978 | Huber | 424/472 |
| 4,341,759 | 7/1982 | Bogentoft et al. | 424/490 |
| 4,594,359 | 6/1986 | Padfield et al. | 514/647 |
| 4,777,033 | 10/1988 | Ikura et al. | 424/488 |
| 4,828,836 | 5/1989 | Elger et al. | 424/499 |
| 4,892,741 | 1/1990 | Ohm et al. | 424/479 |
| 4,933,186 | 6/1990 | Ohm et al. | 424/476 |
| 4,966,772 | 10/1990 | Ohm et al. | 424/482 |
| 5,032,406 | 7/1991 | Dansereau et al. | 424/472 |
| 5,085,865 | 2/1992 | Nayak | 424/472 |
| 5,098,714 | 3/1992 | Wright et al. | 424/473 |
| 5,156,850 | 10/1992 | Wong et al. | 424/473 |
| 5,190,760 | 3/1993 | Baker | 424/480 |
| 5,213,807 | 5/1993 | Chemburkar et al. | 424/472 |
| 5,316,772 | 5/1994 | Jurgens, Jr. et al. | 424/472 |
| 5,601,843 | 2/1997 | Gimet et al. | 424/475 |
| 5,650,169 | 7/1997 | Conte et al. | 424/472 |

FOREIGN PATENT DOCUMENTS

| | | |
|---|---|---|
| 0 299 211 | 1/1989 | European Pat. Off. . |
| 0 384 514 | 8/1990 | European Pat. Off. . |
| 2 120 942 | 12/1983 | United Kingdom . |
| 2 123 291 | 2/1984 | United Kingdom . |
| 2 137 493 | 10/1984 | United Kingdom . |

OTHER PUBLICATIONS

Chemical Abstracts, vol. 90, No. 20, p. 297, 14 May 1979, Columbus, Ohio, USA.
Abstract No. 157017s, Belinda Davis et al., "Diuretic Effect on a Combined Preparation of Frusemide and Slow Release Potassium Chloride".
*Remingtons Pharmaceutical Sciences*, 18$^{th}$ Edition, Mack Publishing Co., Easton Pa. 1990, p. 940.

*Primary Examiner*—Robert H. Harrison
*Attorney, Agent, or Firm*—Burns, Doane, Swecker & Mathis, L.L.P.

[57] ABSTRACT

The invention relates to long-acting pharmaceutical compositions from which the release of the active compound increases exponentially, and to a process for their preparation. The composition, preferably a tablet, comprises a rapid releasing core and a slow-releasing coat surrounding that core.

12 Claims, 3 Drawing Sheets

CONTROLLED RELEASE PHARMACEUTICAL

This application is a continuation of application Ser. No. 08/199,312, filed as PCT/FI92/00242, published as WO93/05769, Apr. 1, 1993, now abandoned.

The invention relates to long-acting pharmaceutical preparations from which the release of the active compound increases exponentially, and to a process for their preparation.

In developing oral long-acting pharmaceutical preparations it is a usual aim to design a preparation which has a constant rate of release of active compound (zero order kinetics). Often such preparations have been made by coating a tablet with a polymer which is insoluble in the intestine and by adjusting the permeability of such coating with a suitable water soluble polymer. The coating process is however expensive and often requires the use of organic solvents.

An easier alternative to coated tablets is a matrix tablet. A matrix tablet is prepared by mixing the active compound with a suitable polymer to produce a uniform mixture. The polymer used is either hydrophobic (insoluble), in which case the active compound is released by diffusion through the pores in the matrix, or hydrophilic (gel forming), in which case the release occurs mainly as the polymer is gradually eroded. In matrix tablets, however, the rate of release usually decreases as a function of time. Typically, the released amount of active compound is proportional to the square root of time or follows primarily first order kinetics.

The attempt to design a long-acting tablet which as close as possible follows zero order kinetics is based on the idea that zero order release result in constant drug levels in the body. The assumption is that absorption conditions in the gastrointestinal tract do not change while the preparation releases active compound. However, this is not always true in oral medical treatment.

When an insoluble tablet is taken orally into the empty stomach, the tablet stays there for 0–2 h. It is then passed through the small intestine in 2–4 hours and is in the lowest part of the small intestine or in the large intestine 2–6 hours after ingestion. Most drugs show greatest absorption in the upper parts of the small intestine, in the duodenum. In the lower part of gastrointestinal tract the absorption decreases and is lowest in the large intestine. This is influenced by the structure and action of gastrointestinal tract as well as the viscosity of the contents of the intestine.

The physiology of the gastrointestinal tract as described above normally means that, if the absorption of drug from a long-acting tablet is wished to be nearly constant, the rate of drug release must increase with time as the tablet moves forward in the gastrointestinal tract, i.e. the release must be exponential.

An attempt for constant absorption (and therefore to zero order release kinetics) is also based on the assumption that medical treatment is optimal when the drug concentration in plasma is as constant as possible during the day. However, numerous diseases are known which have a marked diurnal rhythm. Thus the drug concentration in plasma should also vary in the same rhythm during the treatment.

An example of a disease having a diurnal rhythm is hypertension. Blood pressure is at its lowest at early night and highest early in the morning. Similarly attacks in early morning are typical for pulmonary asthma, and morning stiffness is one symptom of rheumatism and subject to medical treatment. With conventional preparations the plasma concentrations are higher in the early evening than in early morning when the situation should be the opposite. Thus the optimal solution is a long-acting preparation to be taken in the evening and which has a slowly increasing release rate.

U.S. Pat. No. 4,933,186 describes a two layer long-acting tablet with a rapid release core. The purpose of the coat is to delay the release of the active compound from the core. Optionally the coat may be further coated with a layer of active compound. In this case the release is effected in two bursts. Such preparations are not suitable for treatment wherein the active compound must be released in a slowly increasing way.

According to this invention it is possible to prepare simple long-acting oral compositions in which the release of active compound increases as a function of time (exponentially). Characteristically these compositions do not release the active compound discontinuously in bursts but primarily following an exponential release pattern.

According to the invention it is possible to adjust the release of an active compound to the diurnal rhythm of certain diseases. Such diseases are for example hypertension and pulmonary asthma. The compositions according to the invention are also suitable for active compounds which show greater absorption in lower parts of the gastrointestinal tract (e.g. in the large intestine) than in upper parts (e.g. in stomach or the small intestine) or which are designed to act mainly locally in the large intestine. The compositions are suitable for releasing poorly soluble drugs as well as water soluble drugs. Hitherto the formulation of poorly soluble active compounds into long-acting preparations has been especially troublesome. Furthermore the compositions according to the invention are simple and easy to prepare compared to many other long-acting preparations. The preparation process does not require the use of hazardous material, e.g. organic solvents.

The composition according to invention, preferably a tablet, comprises: (a) a core containing an active compound in rapid release form, and (b) a coat surrounding the core, the coat containing an active compound in-slow-release form, wherein 50–99% of the total active compound is in the core.

The core is a conventional rapid release tablet comprising besides an active compound suitable pharmaceutically acceptable auxiliaries, e.g., fillers, lubricants and binders. Examples of such auxiliaries are lactose, polyvinylpyrrolidone, magnesium stearate and talc.

The coat comprises besides an active compound a polymer controlling the rate of release and optionally auxiliaries such as described above. Preferable polymers are hydrophilic, gel forming polymers, especially hydroxypropylmethylcellulose, which is commercially available in various types, e.g., Methocel K100 (m.w. 26000 g/mol), Methocel K4M (m.w. 86000 g/mol), Methocel K15M (m.w. 120000 g/mol) and Methocel K100M. Other hydrophilic polymers include, for example, methylcellulose, hydroxypropylcellulose, sodium carboxymethylcellulose and sodium alginate.

The tablet contains in the core 50–99%, preferably about 55–80%, more preferably about 60–70%, of the total content of active compound. About 30–70%, preferably about 40–60%, of the tablet weight is polymer depending on the desired total release rate. The total tablet diameter is preferably about 7–15 mm.

The release profile may be adjusted on the one hand by the amount and quality of the polymer in the coat, on the other hand by the relative amount of the active compound between the core and the coat. When the active compound is furosemide or salbutamol sulphate, the suitable ratio of active compound between the coat and the core is, for example, 1:2. Suitable polymer amount and type in the coat as well as suitable coat/core ratio for any active compound may be determined by simple dissolution tests described in pharmacopoeias, e.g., the paddle method according to US XXII. The effect of polymer amount and quality in the coat is demonstrated in FIGS. 1 and 3.

The active compound may be a water soluble or poorly soluble compound. When poorly soluble acidic compounds such as furosemide are used, both the core and the coat contain weakly basic inorganic salt, e.g., potassium carbonate. When water soluble active compounds such as salbutamol sulphate are used, no basic salt is needed.

The compositions according to the invention may be prepared easily using conventional tablet-coating press machines. The core may be prepared according to usual tablet processes by pressing powder mixtures or granules. Powders needed for the core are mixed using known powder mixers. The produced mixture may be granulated with the aid of known processes and devices used in preparing tablet mass. The powder mixture may, for example, be moistened with polymer solution or dispersion, e. g., with polyvinylpyrrolidone solution, then sieved into suitable granulate size and dried. Granulation may also be done by spraying powder mixture with solutions or dispersions in fluidized bed granulator. The coat is pressed around the core with the aid of a tablet press or a special tablet-coating press, wherein the coat material may consist of the flowing powder mixtures or granules. The invention is further illustrated with the aid of following examples.

EXAMPLE 1

Figure 1:
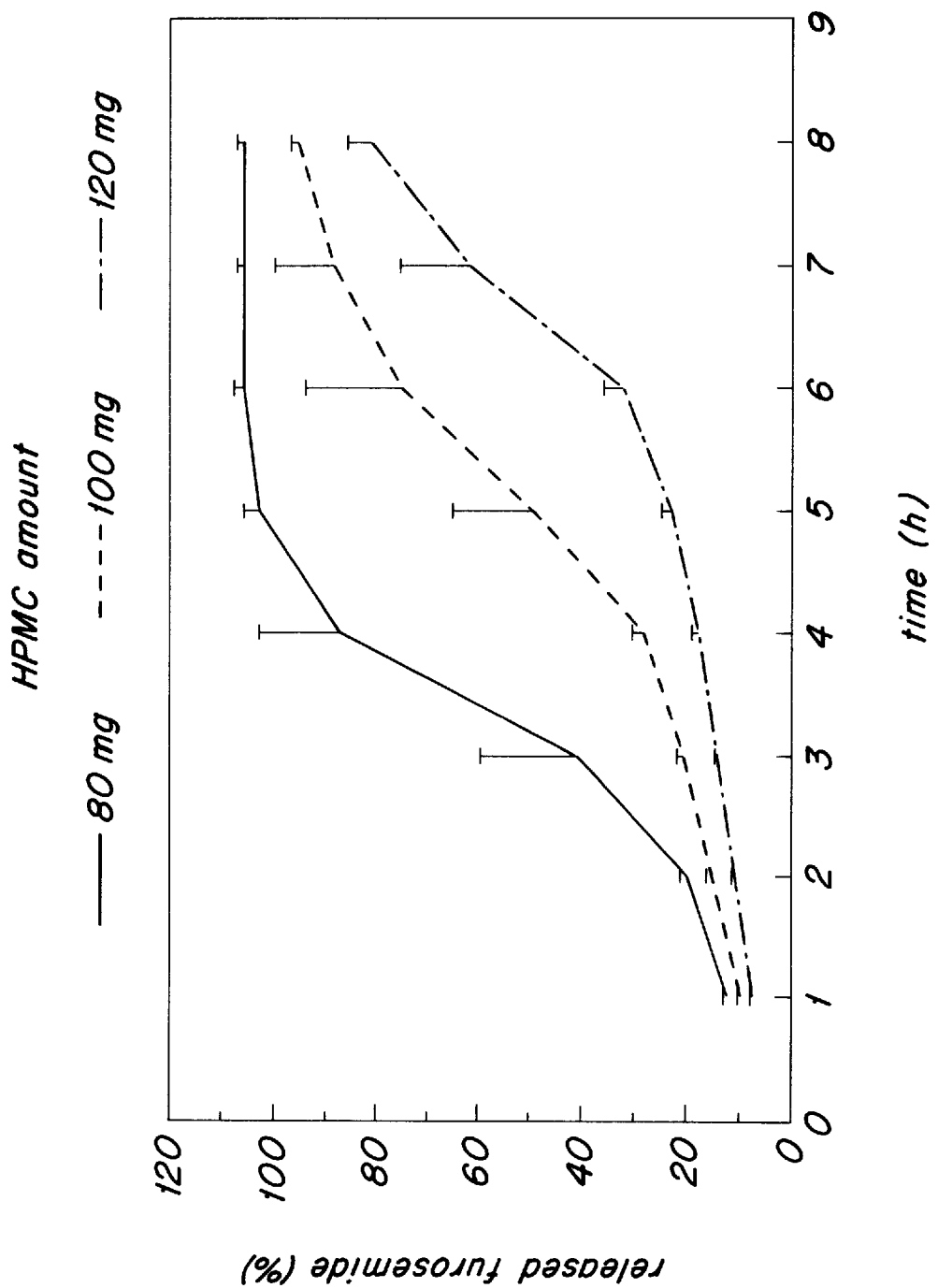
FIG. 1 shows the release of furosemide from the tablets of Examples 1–3. It can be seen that the release curves are primarily exponential up to 80–90% of the total release for all three tablets. Furthermore the figure shows that the position of the release curve may be systematically adjusted with the aid of the polymer amount in the coat.
Figure 2:
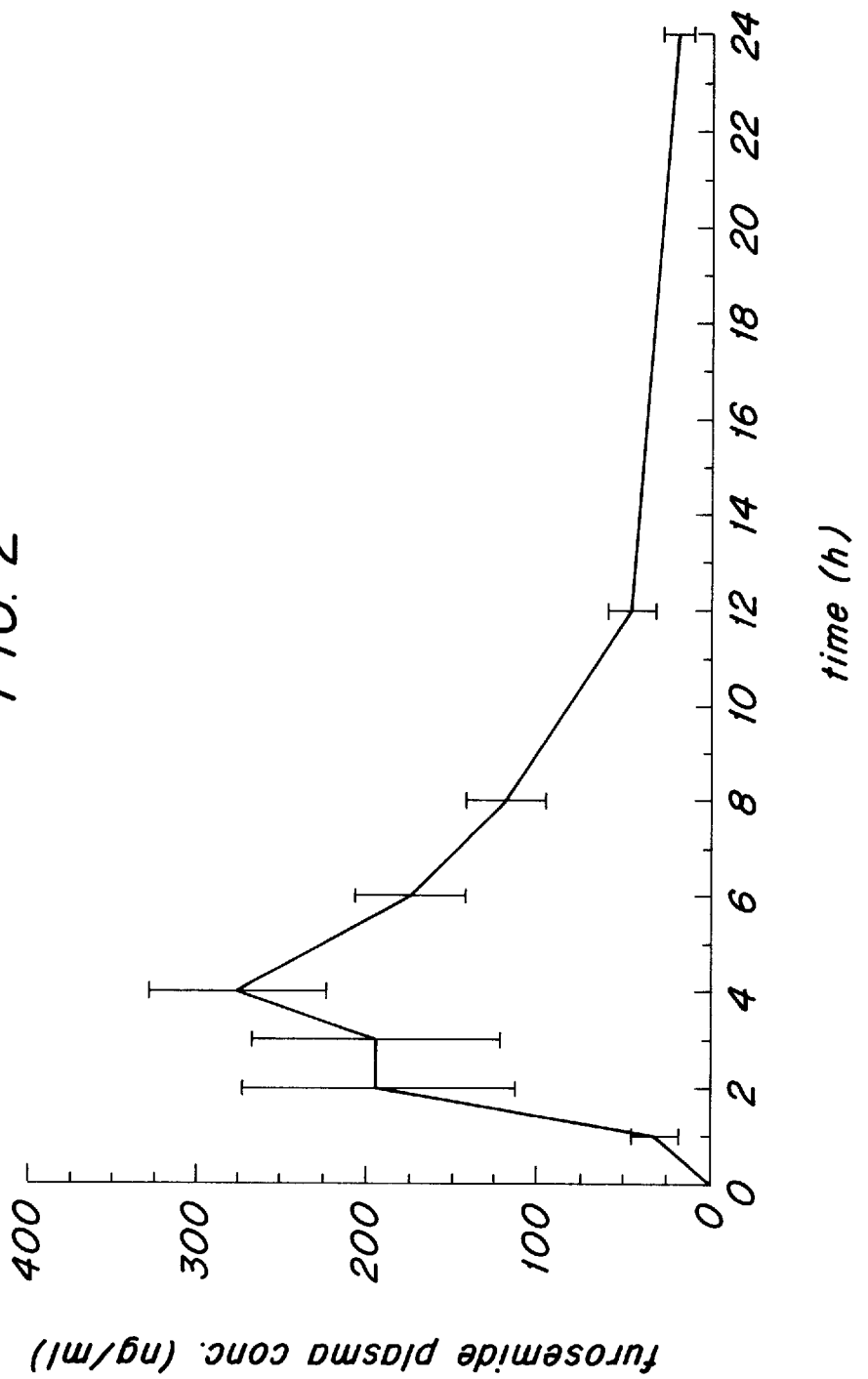
FIG. 2 (tablet of Ex. 2) shows that the compositions according to the invention act as long-acting preparations also in in-vivo conditions. Absorption tests were performed using dogs and furosemide concentrations in plasma were determined by liquid chromatography.
Figure 3:
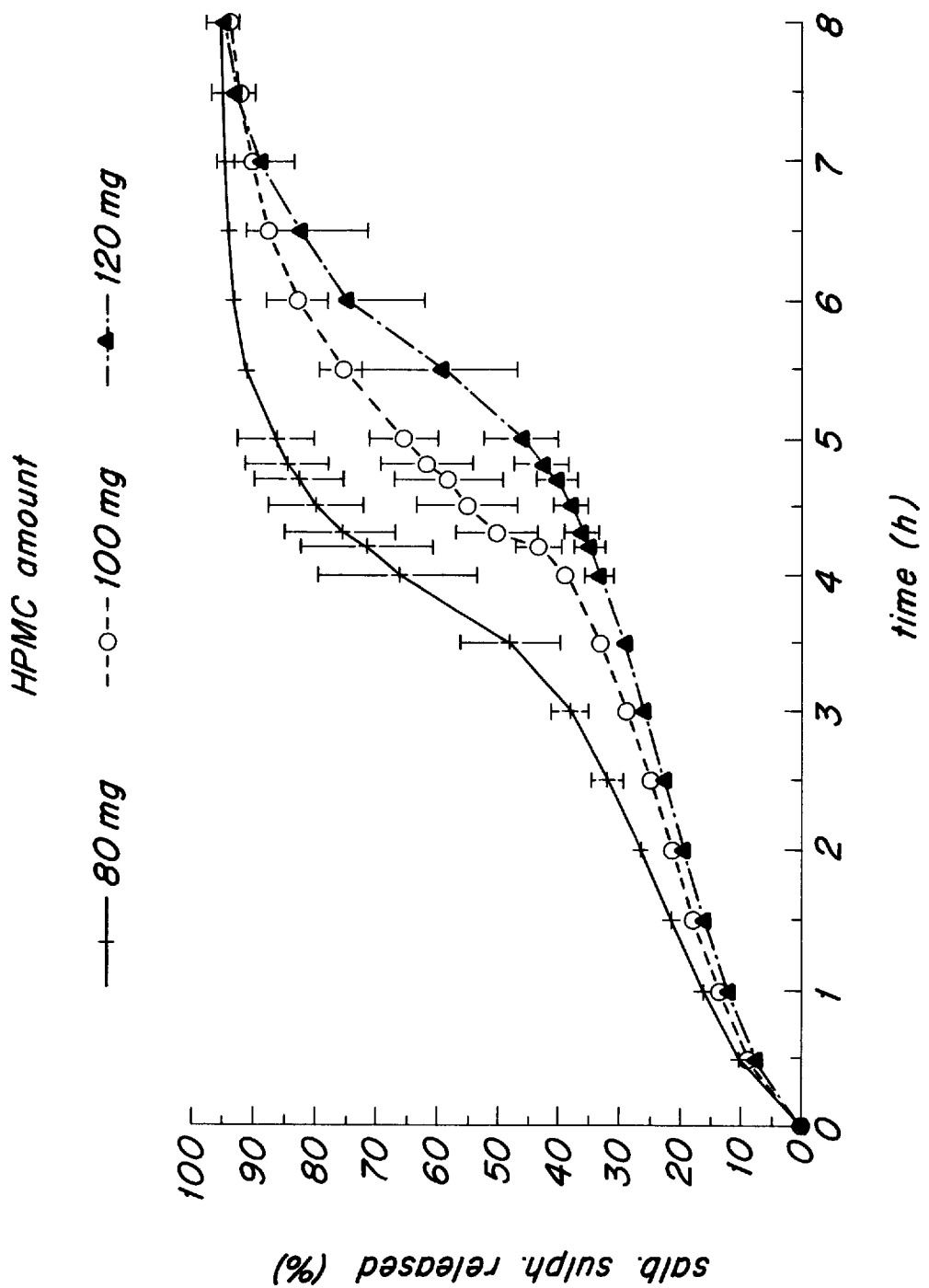
FIG. 3 shows that low soluble drug may be replaced by water soluble drug (here salbutamol sulphate) and nevertheless the release curve remains exponential.

| Core | |
| --- | --- |
| Furosemide | 40 mg |
| Potassium carbonate | 20 mg |
| Lactose | 40 mg |
| Polyvinylpyrrolidone (Kollidon K 25) 10% solution | q.s. |
| Magnesium stearate | 1% |
| Talc | 2% |
| Coat | |
| Furosemide | 20 mg |
| Potassium carbonate | 10 mg |
| Hydroxypropylmethylcellulose (Methocel K100) | 80 mg |
| Magnesium stearate | 1% |
| Talc | 2% |

EXAMPLE 2

As Example 1 but hydroxypropylmethylcellulose amount in the coat is 100 mg.

EXAMPLE 3

As Example 1 but hydroxypropylmethylcellulose amount in the coat is 120 mg.

EXAMPLE 4

| Core | |
| --- | --- |
| Salbutamol sulphate | 16 mg |
| Lactose | 60 mg |
| Polyvinylpyrrolidone (Kollidon K 25) 10% solution | q.s. |
| Magnesium stearate | 1% |
| Talc | 2% |
| Coat | |
| Salbutamol sulphate | 8 mg |
| Hydroxypropylmethylcellulose (Methocel K100) | 80 mg |
| Magnesium stearate | 1% |
| Talc | 2% |

EXAMPLE 5

As Example 4 but hydroxypropylmethylcellulose amount in the coat is 100 mg.

EXAMPLE 6

As Example 4 but hydroxypropylmethylcellulose amount in the coat is 120 mg.

EXAMPLE 7

As Example 4 but the polymer is Methocel K4M.

EXAMPLE 8

As Example 5 but the polymer is Methocel K4M.

EXAMPLE 9

As Example 6 but the polymer is Methocel K4M.

EXAMPLE 10

As Example 4 but the polymer is Methocel K4M and its amount is 160 mg.

The tablets described in the Examples were prepared by mixing powders needed for a batch of desired size in conventional mixers. The powder mixture for the core was moistened with polyvinylpyrrolidone solution and granulated by pressing through a 1.2 mm sieve. Granulate was dried in 30° C. overnight. Dry granulate was sieved and 0.5–1.2 mm fraction was used for pressing tablets using 5–6 mm concave punchs and about 20 kN compressional force. The core tablet was coated with coating material in a tablet press using 9–11 mm concave punchs and 10–15 kN compressional force.

The release of an active compound from tablets may be determined by dissolution tests described in pharmacopoeias, e.g., the paddle method according to US XXII.

I claim:

1. Oral long-acting composition able to release an active compound continuously in the absence of bursts consisting essentially of:

(a) a core which contains an active compound in rapid release form, and (b) a coating surrounding the core, the coating containing an active compound and a release controlling polymer in a uniform mixture, wherein said coating is prepared by mixing the polymer and the active compound together and pressing the resulting homogeneous mixture around the core, and wherein said polymer consisting essentially of a hydrophilic gel forming polymer is selected from the group consisting of hydroxypropylmethylcellulose, hydroxypropylcellulose, methyl cellulose, sodium carboxymethylcellulose and sodium alginate, and wherein 55 to 99% of the total active compound is in the core and 30–70% of the total composition weight is polymer.

2. A composition according to claim 1, wherein the polymer is hydroxypropylmethylcellulose.

3. A composition according to claim 2, wherein the molcular weight of the hydroxypropylmethylcellulose is 20000–150000 g/mol.

4. A composition according to claim 1, wherein about 55–80%, of the total active compound is in the core.

5. A composition according to claim 1, wherein the active compound is a poorly water soluble weak acid.

6. A composition according to claim 5, wherein the composition also comprises potassium carbonate.

7. A composition according to claim 1, wherein the active compound is furosemide.

8. A composition according to claim 1, wherein the active compound is a water soluble salt.

9. A composition according to claim 8, wherein the active compound is salbutamol sulphate.

10. A composition according to claim 1, wherein the composition is a two layer tablet.

11. A composition according to claim 1, wherein about 60–70% of the total active compound is in the core.

12. A composition according to claim 1, wherein about 40 to 60% of the total composition weight is polymer.

* * * * *